United States Patent [19]
Giles et al.

[11] 4,182,920
[45] Jan. 8, 1980

[54] PROCESS FOR HYDRATION OF OLEFINS TO PRODUCE ALCOHOLS

[75] Inventors: James H. Giles, Lake Jackson; Jeffery H. Stultz, Freeport; Sandra W. Jones, Lake Jackson, all of Tex.

[73] Assignee: The Dow Chemical Company, Midland, Mich.

[21] Appl. No.: 814,363

[22] Filed: Jul. 11, 1977

[51] Int. Cl.$^2$ .............................................. C07C 29/04
[52] U.S. Cl. ................................ 568/895; 568/898; 568/899
[58] Field of Search ............... 260/641; 568/895, 898, 568/899

[56] References Cited

U.S. PATENT DOCUMENTS

| | | | |
|---|---|---|---|
| 3,257,469 | 6/1966 | Kovach | 260/641 |
| 3,801,656 | 4/1974 | Frampton et al. | 260/641 |
| 4,096,199 | 6/1978 | Moy et al. | 568/899 |

FOREIGN PATENT DOCUMENTS

| | | | |
|---|---|---|---|
| 50-30602 | 6/1975 | Japan | 260/641 |
| 1374368 | 11/1974 | United Kingdom | 260/641 |

*Primary Examiner*—Joseph E. Evans
*Attorney, Agent, or Firm*—A. C. Ancona

[57] ABSTRACT

An improved process for making an alcohol by hydration of an olefin in the presence of a cation exchange resin in the acid form as catalyst and in the presence of a solvent for the reactants and product alcohol, wherein the solvent and reactants are introduced to the reactor as a single homogeneous phase to a first-stage reactor. Part of the olefin is added to a second-stage reactor. The effluent from the second stage is passed to a third-stage reactor and the unreacted olefin and solvent from the third-stage effluent are recycled to the first-stage reactor after removal of substantially all of the product alcohol. The process provides improved conversions and yields and enables the use of smaller amounts of solvent.

1 Claim, 1 Drawing Figure

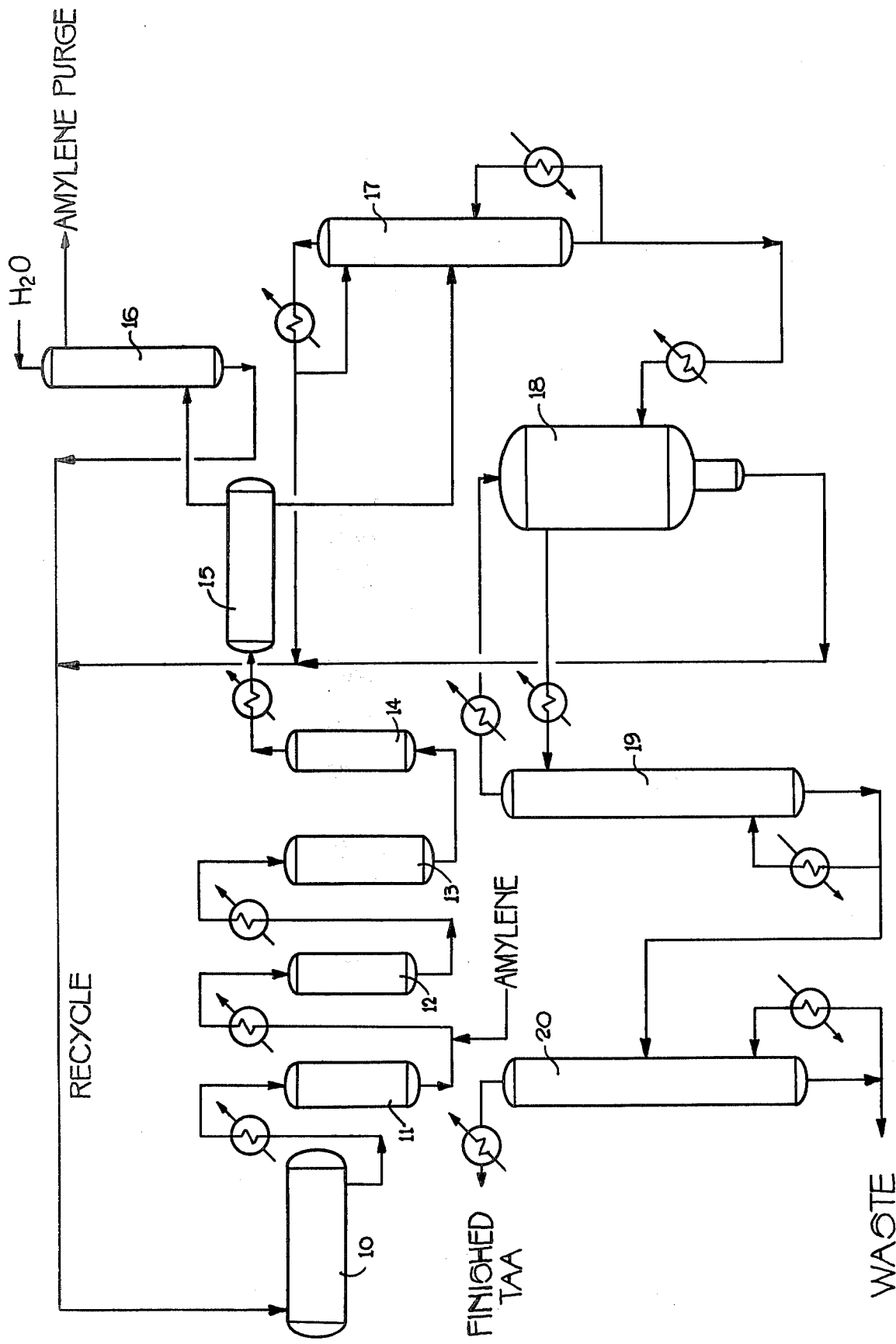

PROCESS FOR HYDRATION OF OLEFINS TO PRODUCE ALCOHOLS

BACKGROUND OF THE INVENTION

It is known to react water and an olefin in the presence of an acid catalyst and to employ a synthetic organic cation exchange resin in the acid form as that catalyst. Early patent references suggest that the water be maintained in the liquid phase. Specifically, U.S. Pat. No. 2,477,380 teaches that, while the water must be maintained in the liquid phase, it makes no difference whether the olefin is in the liquid or vapor phase. Another which teaches the necessity of maintaining the water of reaction at least partly in the liquid phase is U.S. Pat. No. 2,813,908.

More recently it has been taught that it is useful to employ a solvent which has solvency for both reactants—the water and the olefin. The solvent enhances the rate of hydration of forming solutions with the olefin and with the water, in each of which the product alcohol is soluble. This prevents the accumulation of the product alcohol at the catalyst surface and allows the reaction to approach equilibrium.

Solvents suggested for the purpose are oxygen-containing compounds, for example alcohols, ethers and ketones. Isopropyl alcohol, ethyl ether and acetone, among others, are specifically mentioned in U.S. Pat. No. 3,257,469. Separate phases of product alcohol-water-solvent and product alcohol-olefin-solvent are taught to be necessary in U.S. Pat. No. 3,285,977. Each of these phases is homogeneous, but immiscible with the other.

The present invention employs a single, homogeneous phase of olefin, water and solvent as the feed to the first stage of a three-stage reactor system and maintains the homogeneity throughout the course of the reaction. A further aspect of the invention is to feed less than all of the olefin to the first stage reactor and to feed the remainder into the second stage reactor, thereby decreasing the amount of solvent required. The product alcohol acts as a cosolvent together with the solvent added with the feed.

SUMMARY OF THE INVENTION

The invention is a process for the hydration of olefins to produce alcohols in the presence of an acid cation exchange resin catalyst and in the presence of a solvent for the reactants and product alcohol, wherein the improvement comprises introducing the reactants and solvent as a single phase into a first reactor, introducing additional olefin together with the effluent from the first reactor to a second reactor, introducing the effluent from the second reactor to a third reactor and subsequently removing the product alcohol from the effluent of the third reactor and recycling the unreacted olefin and solvent to the first reactor. The improved process is particularly useful in the hydration of isoamylenes (2-methyl butenes) wherein acetone is employed as a solvent.

DETAILED DESCRIPTION OF THE INVENTION

The olefins useful in the present process are those having from about four to eight carbon atoms. In particular the process will be described in terms of an amylene feed. Amylenes available commercially contain by weight about 84 percent 2-methyl butene-2, about 8 percent 2-methyl butene-1, and about 2–3 percent pentanes; minor amounts of $C_4$ to $C_6$ hydrocarbons, (both saturated and unsaturated) and some unknown heavier components make up the remainder of the feed. Both isomers of amylene mentioned above, and which account for 92 percent of the commercial feedstock, are convertible to the t-amyl alcohol (1,1-dimethyl propanol).

The unreactive aliphatic hydrocarbon components e.g pentane, and pentadiene, are continually introduced in the fresh amylene feed, but are not removed with the product alcohol. Thus, to prevent their accumulation a purge system is employed in which a small amount of the third-stage reactor effluent is flash distilled, condensed and washed to remove the acetone, which is 60% of the condensed stream. The hydrocarbon part of the purge stream is then sent to storage for subsequent disposal. The acetone and water stream is recycled to the feed tank to the first reactor.

Small amounts of formic and acetic acid are also found in the reactor effluent which must not be allowed to build up and recirculate in the system. In order to remove these acid components a bed of anion exchange resin in the base ($OH^-$) form is installed immediately following the third-stage reactor. This effectively removes the acid and allows the use of carbon steel, rather than a more expensive acid resistant material, to be used throughout the system.

Solvents found to be useful in the present invention are those alcohols and ketones having boiling points below 100° C. Thus, methyl, ethyl and propyl (both primary and secondary) alcohols and dimethyl, methyl ethyl and methyl isopropyl ketones are suitable. Especially preferred are acetone and isopropyl alcohol, with the former being most preferred. Although less of the isopropyl alcohol (by weight) is required in the feed to attain homogeneity, the acetone offers advantages in the finishing end of the process and the volume of by-products derived from the solvent is less when employing acetone.

Temperatures employed in the reaction are from about 30°–80° C. Higher or lower temperature may be employed, but at the sacrifice of reaction rate, at lower temperatures and conversion at equilibrium at the higher temperatures. It is preferred to run the first reactor at a temperature in the range of from 70°–80° C. to take advantage of faster reaction rates, while the second and third reactors are run within the ranges of 60°–70° C. and 40°–60° C., respectively, because of a more favorable equilibrium at the lower temperatures.

Pressure employed is sufficient to keep all components in the liquid phase, but is generally between 65 and 200 psia. More pressure can be tolerated but is of no particular benefit.

The improved process comprises the steps of feeding from a mixing tank a homogeneous single phase solution of amylene (including unreactive hydrocarbon components), water, and solvent, e.g. acetone, to a first reactor containing as catalyst a bed of cation exchange resin in the acid ($H^+$) form. Some of the amylene is converted to t-amyl alcohol and the effluent of the first reactor is mixed with additional amylene and passed to a second reactor of substantially the same volume as the first and containing a like amount of the same catalyst. The effluent of the second reactor is then passed to a third reactor of approximately twice the volume of the first two reactors and containing the catalyst in an amount about equal to the sum of the catalyst in the first two reactors.

The effluent from the third reactor is then passed through a bed of anion exchange resin in the base (OH$^-$) form to remove small amounts of acid formed as by-product. Following the acid removal the product stream is sent to a flash distillation in which up to about 10% of the stream is taken overhead. This cut, consisting of about 60% solvent (acetone) and 40% amylene, is condensed and fed to a wash column wherein it is washed with water to remove the acetone. The acetone and water are recycled to the feed mixing tank and the amylene portion, containing some unreactive components is removed from the system. The flash and wash steps form the purge system which prevent the build-up of the unreactive components of the amylene feed which are not removed with the product alcohol.

The major portion (90% or more) of the product stream, taken from the bottom of the flash distillation is sent to a distillation column in which the acetone solvent, together with unreacted amylene and a small amount of t-amyl alcohol are taken overhead. This stream is condensed and combined with the water and acetone from the wash column of the purge system and returned to the mixing tank.

The final steps in the process are the drying and purification of the t-amyl alcohol. The wet alcohol is sent to a phase separation vessel which is charged with amylene to aid in the separation. Amylene, being more soluble in the alcohol than is the water, helps phase-out the water dissolved in the alcohol. The alcohol, still containing some water, is then sent to an azeotropic distillation which removes small quantities of the alcohol with the water overhead and the dry alcohol forms a bottom stream. The amylene flashes overhead in the drying column, is condensed and then recycled to the phase separator. Sufficient amylene is charged originally to the phase separator to provide from about 30 to about 50% by volume of the feed to the drying column. No additional amylene is required during the course of the process since none is lost. The overhead azeotrope is condensed and separated, the water being recycled to the mixing tank while the t-amyl alcohol is sent back to the phase separation for feed to the azeotropic drying column. The dry alcohol is then sent to the distillation column where heavy impurities are removed. The purified t-amyl alcohol is condensed from the overhead stream of the still and the impurities in the bottom are discarded.

A pilot plant reactor, made of 304 stainless steel pipe, 8″ in diameter and having a volume of 1.1 ft.$^3$, was filled with 1 ft.$^3$ Dowex Ⓡ MSC-1 resin beads (a cation exchange resin available from The Dow Chemical Co.) previously treated to convert them to the acid (H$^+$) form. This reactor was employed to conduct the reaction of isoamylene and water. The three-reactor process of the present invention was simulated by passing a particular batch of feed through the column, collecting the effluent and passing this again through the column after adjusting the composition to provide for the addition of amylene to the second reactor. Finally, this effluent was passed through the reactor the third time to complete the three-stage process.

In a typical run, a feed mixture was prepared in a mixing tank. The feed was thoroughly mixed, checked for homogeneity, and then transferred to the reactor feed tank. The feed was pumped from the feed tank through a heat exchanger to the reactor. The feed to the reactor was maintained at a constant temperature by varying the steam flow rate through the preheater. Feed to the reactor was kept at a constant rate by pneumatic adjustment of the stroke of the pump. Constant pressure was maintained by controlling the effluent rate through a pressure let-down valve. The reactor effluent was cooled to ambient and collected in a receiver tank. All flow rates were obtained by the use of the weighcell system. Data collected included temperatures throughout the reactor, reactor pressure, feed rate, and feed and effluent compositions.

In all runs involving the previously described three-reactor system, it was necessary to collect the effluent from each reactor pass in drums. Upon completion of each pass, the contents were charged back to the mixing tank. The feed composition was adjusted as necessary prior to the second pass through the reactor.

EXAMPLE 1

The following data is representative of that obtained according to the preceding method:

| 1$^{st}$ Reactor Conditions: | LHSV* = 0.138 hr.$^{-1}$ Temp. (°C.) = 70 Mole ratio (water/amylene**) = 4.60/1 | |
|---|---|---|
| | | Weight Percent |
| Component | Feed | Effluent |
| Water | 10.88 | 10.21 |
| Reactive Amylene | 9.20 | 6.53 |
| Non-reactive Amylene | 7.07 | 7.07 |
| Acetone | 72.19 | 72.19 |
| t-Amyl Alcohol | 0.66 | 4.00 |
| 2$^{nd}$ Reactor Conditions: | LHSV = 0.21 hr.$^{-1}$ Temp. (°C.) = 60 Mole ratio (water/amylene) = 2.30 | |
| | | Weight Percent |
| Component | Feed | Effluent |
| Water | 9.17 | 7.99 |
| Reactive Amylene | 15.52 | 10.80 |
| Non-reactive Amylene | 6.86 | 6.86 |
| Acetone | 64.85 | 64.85 |
| t-Amyl Alcohol | 3.60 | 9.50 |
| 3$^{rd}$ Reactor Conditions: | LHSV = 0.075 hr.$^{-1}$ Temp. (°C.) = 50 Mole ratio (water/amylene) = 2.88 | |
| | | Weight Percent |
| Component | Feed | Effluent |
| Water | 7.99 | 7.46 |
| Reactive Amylene | 10.80 | 8.93 |
| Non-reactive Amylene | 6.86 | 6.86 |
| Acetone | 64.85 | 64.85 |
| t-Amyl Alcohol | 9.50 | 11.90 |

The yield of t-amyl alcohol, based on reactive amylene fed, was 93%.
*LHSV liquid hourly space velocity based on reactive amylene present
**mole ratio is based on reactive amylene present A preferred procedure is given in the following description which refers to the drawing and the numbers employed thereon.

From the mixing tank 10 is fed a single phase solution containing acetone, water and small amounts of recycled t-amyl alcohol and amylene, via a heat exchanger, to the first stage reactor 11. The effluent is mixed with amylene and the resulting solution sent through another heat exchanger and thence to the second stage reactor 12. The effluent from the second stage then passes through yet another heat exchanger and into the third stage reactor 13. The effluent from the third stage is then passed through a bed of anion exchange resin 14 which removes small amounts of acid from the product stream. Following the acid removal the product stream is heated and flash distilled in vessel 15 from which about 3–5% is sent overhead and thence to a wash column 16 to recover the acetone. Water and acetone from the bottom of wash column 16 are sent back to the mixing tank 10 and a small amount of amylene together with unreactive $C_5$'s is purged from the system and burned. The bottoms (95–97% of the stream) from flash vessel 15 are sent to column 17 to recover solvent and unreacted amylene which are distilled overhead, condensed and combined with the acetone and water from the bottom of the wash column 16 and returned to the mixing tank 10 for recycling. The bottoms of the solvent recovery column 17 are cooled further and sent to a phase separator 18, where the water forms a lower phase (with the aid of the presence of a $C_5$ hydrocarbon) and is returned to the mixing tank. The t-amyl alcohol product (upper phase) is then sent from the phase separator 18 to an azeotropic drying column 19 where a part of the alcohol azeotropes with the water to remove it in an overhead stream which is condensed and returned to the phase separator. The dried alcohol containing heavy impurities (primarily solvent-derived by-products), is sent to a finishing column 20 in which the pure product alcohol is taken overhead and the heavy impurities remain in the bottoms.

The following two examples are continuous plant runs in which three reactors were connected in series. The bulk of the amylene was fed to the second reactor (only amylene in the recycle stream being fed to the first reactor) and the purge, drying and finishing systems were included as part of the total process system as described above.

EXAMPLE 2

1st Reactor Conditions: LHSV = 0.075 hr.$^{-1}$ Temp. (°C.) = 68
Mole ratio (water/amylene) = 4.36

| Component | Weight Percent | |
|---|---|---|
| | Feed | Effluent |
| Water | 11.88 | 10.62 |
| Amylene* | 13.26 | 8.86 |
| Acetone | 69.03 | 68.57 |
| TAA** | 1.10 | 6.66 |
| Balance | 4.73 | 5.29 |

2nd Reactor Conditions: LHSV = 0.135 hr.$^{-1}$ Temp. (°C.) = 59
Mole ratio (water/amylene) = 2.17

| Component | Weight Percent | |
|---|---|---|
| | Feed | Effluent |
| Water | 9.32 | 7.96 |
| Amylene | 20.05 | 13.88 |
| Acetone | 60.16 | 60.16 |
| TAA | 5.84 | 13.14 |
| Balance | 4.63 | 4.86 |

3rd Reactor Conditions: LHSV = 0.044 hr.$^{-1}$ Temp. (°C.) = 35
Mole ratio (water/amylene) = 2.80

| Component | Weight Percent | |
|---|---|---|
| | Feed | Effluent |
| Water | 7.96 | 7.36 |
| Amylene | 13.88 | 12.44 |
| Acetone | 60.16 | 59.80 |
| TAA | 13.14 | 15.58 |
| Balance | 4.86 | 4.82 |

TAA yield, based on reactive amylene fed was 88%.
*Amylene feed consisted of both reactive and unreactive components
**TAA = t-amyl alcohol

EXAMPLE 3

1st Reactor Conditions: LHSV = 0.043 Temp. (°C.) = 68
Mole ratio (water/amylene) = 4.42

| Component | Weight Percent | |
|---|---|---|
| | Feed | Effluent |
| Water | 10.28 | 9.59 |
| Amylene | 12.09 | 6.46 |
| Acetone | 73.99 | 74.49 |
| TAA | 0.47 | 5.82 |
| Balance | 3.17 | 3.64 |

2nd Reactor Conditions: LHSV = 0.082 Temp. (°C.) = 58
Mole ratio (water/amylene) = 2.39

| Component | Weight Percent | |
|---|---|---|
| | Feed | Effluent |
| Water | 8.41 | 7.64 |
| Amylene | 17.22 | 11.20 |
| Acetone | 66.00 | 66.00 |
| TAA | 5.15 | 11.34 |
| Balance | 3.22 | 3.82 |

3rd Reactor Conditions: LHSV = 0.022 Temp. (°C.) = 47
Mole ratio (water/amylene) = 3.54

| Component | Weight Percent | |
|---|---|---|
| | Feed | Effluent |
| Water | 7.64 | 7.08 |
| Amylene | 11.20 | 10.38 |
| Acetone | 66.00 | 65.14 |
| TAA | 11.34 | 13.46 |
| Balance | 3.82 | 3.94 |

TAA yield, based on reactive amylene, was 91.2%.

We claim:

1. A process for making t-amyl alcohol by reacting 2-methyl butenes, contained in a $C_5$ hydrocarbon mixture, with water, employing acetone as a solvent, in the presence of the acid form of a cation exchange resin in a three-stage reactor system which comprises, (1) feeding said $C_5$ hydrocarbon mixture into the effluent of the first stage reactor which contains water, acetone, recycle 2-methyl butenes, t-amyl alcohol product, unreactive hydrocarbons and by-products as a single phase solution, (2) passing said mixture as a single phase solution into a second stage reactor and from thence into a third stage reactor, (3) treating the effluent of said third stage reactor to remove acidic impurities formed in the process by passing said effluent through a bed of anion exchange resin in the base form, (4) distilling the effluent of said anion exchange resin bed to flash overhead up to about 10 percent by weight of the so-treated effluent to remove a part of the unreactive hydrocarbons contained therein, (5) condensing and recovering acetone from the flashed overhead portion by contacting with water and returning the acetone and water to the feed to the first stage reactor, (6) distilling the bottoms from step 4 to recover overhead the acetone along with unreacted 2-methylbutenes, (7) condensing the acetone and unreacted 2-methyl-butenes and returning same to the feed to the first stage reactor, (8) treating the bottoms from step 6, which contains the product alcohol, water and higher boiling by-products, to phase separate at least part of the water by adding a $C_5$ hydrocarbon mixture, (9) separating the alcohol phase and azeotropically distilling to dry the alcohol,

(10) recovering the alcohol from the distillate and returning it to the azeotropic distillation and returning the water to the feed to the first stage reactor,

(11) passing the dry alcohol contained in the bottoms of said azeotropic distillation which contains higher boiling by-products to a distillation column and distilling to recover the pure t-amyl alcohol.

* * * * *